United States Patent

O'Lenick, Jr. et al.

Patent Number: 5,786,389
Date of Patent: Jul. 28, 1998

[54] GUERBET CASTOR ESTERS

[75] Inventors: Anthony J. O'Lenick, Jr., Lilburn; Jeffrey K. Parkinson, Dacula, both of Ga.

[73] Assignees: Lambert Technologies Inc., Norcross, Ga.; Hanson Co., Woodbury, N.Y.

[21] Appl. No.: 980,432

[22] Filed: Dec. 28, 1997

[51] Int. Cl.$^6$ .................................................. A01N 37/00
[52] U.S. Cl. .......................... 514/552; 514/546; 514/549; 554/213
[58] Field of Search ................................ 514/546, 549, 514/552; 554/213

[56] References Cited

U.S. PATENT DOCUMENTS 4,425,458  1/1984  Lindner et al. .
4,868,236  9/1989  O'Lenick, Jr. .

Primary Examiner—Gary Geist
Assistant Examiner—Deborah D. Carr

[57] ABSTRACT

The present invention deals with the certain castor esters which give high gloss when applied to the skin. Said esterd are the reaction of a guerbet alcohol and castor oil, ricinoleic acid or methyl ricinoleate.

9 Claims, No Drawings

GUERBET CASTOR ESTERS

BACKGROUND OF THE INVENTION

1. Field of the Invention

The present invention deals with the use of certain novel esters which are prepared by the reaction of a guerbet alcohol and castor oil, castor fatty acid or castor methyl ester. Specifically the present invention describes a process for providing gloss to the skin which comprises application of an effective glossing concentration of an ester made by reacting castor and guerbet alcohols.

2. Description of the Art Practices

Guerbet alcohols have been known for many years. Over the years there have been a number of derivatives patented.

U.S. Pat. No. 4,868,236 to O'Lenick discloses a guerbet citric ester and polymers thereof useful in plastic lubrication.

U.S. Pat. No. 4,425,458 to Lindner and O'Lenick teaches that specific guerbet esters can be used as polycarbonate lubricants.

There is a desire to develop an ester that gives gloss to the skin when applied from oils or applied form emulsions.

Until the compounds of the present invention esters did not give a sufficient gloss when applied to thex skin. None of the prior esters possess the critical combination of guerbet branching and the hydroxyl containing unsaturated group unique to castor.

THE INVENTION

This invention relates to the gloss properties of a particular group of highly branched, unsaturated esters made by the reaction of a guerbet alcohol and castor oil, ricinoleic acid or methyl ricinoleate.

The unique structure of the ricinoleic moiety from castor oil coupled with the proper selection of the guerbet alcohol chosen to make the ester that has unique gloss when applied to skin. Specifically, the present invention discloses a process for providing gloss to the skin which comprises application of an effective glossing concentration of an ester conforming to the following structure:

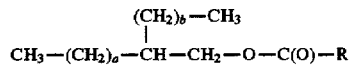

wherein;

a and b are independently integers ranging from 4 to 20; and R is $CH_3—(CH_2)_5—CH(OH)—CH_2—CH=CH—(CH_2)_7—$.

The products are applied to skin in the form of oils phases or emulsions at a concentration of between 1% and 25% by weight based upon the weight of the total formula.

PREFERRED EMBODIMENT

In a preferred embodiment a and b are each 8.

In a preferred embodiment a, b are each 6.

In a preferred embodiment a, b are each 4.

In a preferred embodiment a, b are each 10.

In a preferred embodiment a, b are each 20.

In a preferred embodiment the effective glossing concentration is between 1% and 25% by weight.

In another preferred embodiment the effective glossing concentration is between 1% and 15% by weight.

In another preferred embodiment the effective glossing concentration is between 2% and 10% by weight.

EXAMPLES

RAW MATERIALS

Guerbet Alcohols

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

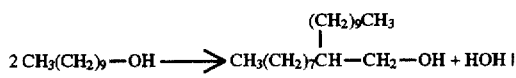

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the guerbet process gives essentially 100% product.

Guerbet alcohols that are the reaction product of one specific raw material alcohol will result in a so called "homo-guerbet". In this case R and R' are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

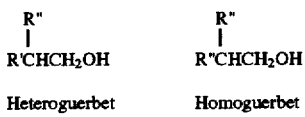

Guerbet alcohols are available commercially from Nova Molecular Technologies Janesville, Wis. They are marketed under the following commercial names:

| Example | Commercial Name | a | b |
|---|---|---|---|
| 1 | Nova Guerbet C10 | 3 | 3 |
| 2 | Nova Guerbet C12 | 4 | 4 |
| 3 | Nova Guerbet C14 | 5 | 5 |
| 4 | Nova Guerbet C16 | 6 | 6 |
| 5 | Nova Guerbet C18 | 7 | 7 |
| 6 | Nova Guerbet C20 | 8 | 8 |
| 7 | Nova Guerbet C32 | 14 | 14 |

Castor Oil

Castor oil is a unique triglyceride. It is derived from *Ricinus Communis L.* The castor plant grows wild in many subtropical and tropical areas. Today Brazil, China and India provide over 90% of the oil. Castor oil contains a large content of hydroxy containing compounds that are unsaturated. The common name for the predominant species in castor is ricinoleic acid. More correctly it is called 12-hydroxy-9 octadecenoic acid or d-12-hydroxyoleic acid. The acid conforms to the following structure:

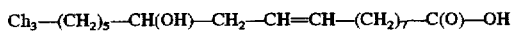

$$CH_3-(CH_2)_5-CH(OH)-CH_2-CH=CH-(CH_2)_7-C(O)-OH$$

Castor Oil is a clear, viscous, light colored fluid that is nondrying and quite stable. The Purity of Castor Oil occurs with remarkable uniformity. Regardless of country of origin, or season it is grown, the composition and chemical properties remain within a very narrow range. Castor Oil has a CAS Number of 8001-79-4 and an EINECS Number of 232-293-8.

Castor oil has a unique carbon distribution, which has 18 carbon atoms and one double bond. The concentration of that species is about 90% by weight. It is this ricinoleic moiety that when linked to a guerbet alcohol in an ester gives unique gloss when applied to the skin.

Ricinoleic acid has the unusual property of having both a double bond, that results in a specific conformation of the "kinked carbon chain" placing the hydroxyl group in a locked position. While not professing only one mechanism of action, it is believed that the introduction of the polar guerbet branched portion of the molecule results in an ester that has a great deal of branching. The molecule takes on a conformation having the minimum free energy. That conformation places the polar hydroxyl groups from different molecules into an associative complex. This complex is delivered to the skin either neat or in emulsions giving a great deal of gloss that is durable. There are many cosmetic applications in which gloss is desirable.

Ester Synthesis

The esterification reaction is carried out using an excess of alcohol or castor or more typically using an equivalent of each. The esterification reaction can be carried out with or without catalyst, however when no catalyst is used the reaction times are protracted. Catalysts like benzene sulfonic acid, tin, sulfuric acid, tin salts and the like can be used. The most satisfactory catalyst is stannous oxylate.

General Procedure—Castor oil

To the specified number of grams of guerbet alcohol (examples 1–7) is added then 300.0 grams of castor oil. Next add 0.1% stannous oxylate based upon the total weight of the batch after all ingredients have been charged, under agitation. The temperature of the mass is raised to 150°–200° C. and glycerine is stripped off under vacuum. The acid value and hydroxyl value drop to vanishingly small values, and the saponification value increases to theoretical.

The products are clear liquids. The glycerine produced using the castor oil is decanted off after the product cools, the use of the ricinoleic acid or methyl ricinoleate results in the formation of water and methanol respectively, which are distilled off.

| Example | Guerbet Alcohol Example | Grams |
|---|---|---|
| 8 | 1 | 157.0 |
| 9 | 2 | 185.0 |
| 10 | 3 | 213.0 |
| 11 | 4 | 241.0 |
| 12 | 5 | 269.0 |

-continued

| Example | Guerbet Alcohol Example | Grams |
|---|---|---|
| 13 | 6 | 297.0 |
| 14 | 7 | 465.0 |

General Procedure—Ricinoleic Acid

To the specified number of grams of guerbet alcohol (examples 1–7) is added then 300.0 grams of ricinoleic acid. Next add 0.1% stannous oxylate based upon the total weight of the batch after all ingredients have been charged, under agitation. The temperature of the mass is raised to 180°–200° C. and water is stripped off under vacuum. The acid value and hydroxyl value drop to vanishingly small values, and the saponification value increases to theoretical.

| Example | Guerbet Alcohol Example | Grams |
|---|---|---|
| 15 | 1 | 157.0 |
| 16 | 2 | 185.0 |
| 17 | 3 | 213.0 |
| 18 | 4 | 241.0 |
| 19 | 5 | 269.0 |
| 20 | 6 | 297.0 |
| 21 | 7 | 465.0 |

Applications Examples

Series 1

The esters of the present invention were added to soybean oil at 1 5 and 25% by weight. 0.5 ml of the resulting mixture was applied to the back of the hand. The gloss was rated on a scale of 0–5. 0 being no gloss 5 being high gloss.

| | Gloss Rating | | |
|---|---|---|---|
| | 1% | 10% | 25% |
| Compound of the Invention | | | |
| Example 20 (octyldodecyl ricinoleate) | 5 | 5 | 5 |
| Example 19 | 4 | 4 | 5 |
| Other Compounds | | | |
| octyldodecyl meadowfoamate | 2 | 2 | 3 |
| octyldodecyl stearate | 1 | 1 | 2 |
| tri-octyldodecyl citrate | 1 | 1 | 2 |
| Soybean oil | 0 | 0 | 1 |

Series 2

The esters of the present invention were added emulsified into water using non-ionic surfactants. oil at 1, 5 and 25% by weight. 0.5 ml of the resulting mixture was applied to the back of the hand. The gloss was rated on a scale of 0–5. 0 being no gloss 5 being high gloss.

| | Gloss Rating | | |
|---|---|---|---|
| | 1% | 10% | 25% |
| Compound of the Invention | | | |
| Example 20 (octyldodecyl ricinoleate) | 4 | 4 | 5 |
| Example 19 | 4 | 4 | 4 |

|  | Gloss Rating | | |
| --- | --- | --- | --- |
|  | 1% | 10% | 25% |
| Other Compounds | | | |
| octyldodecyl meadowfoamate | 2 | 2 | 3 |
| octyldodecyl stearate | 1 | 1 | 2 |
| tri-octyldodecyl citrate | 1 | 1 | 2 |
| Soybean oil | 0 | 0 | 1 |

As the data clearly shows, the gloss is achieved using the ricinoleic derivative only.

What is claimed:

1. A process for providing gloss to the skin which comprises application of an effective glossing concentration of an ester conforming to the following structure:

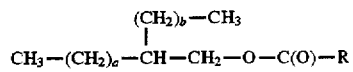

a and b are independently integers ranging from 4 to 20; and

R is $CH_3$—$(CH_2)_5$—$CH(OH)$—$CH_2$—$CH=CH$—$(CH_2)_7$—.

2. A process of claim 1 wherein a and b are each 8.
3. A process of claim 1 wherein a, b are each 6.
4. A process of claim 1 wherein a, b are each 4.
5. A process of claim 1 wherein a, b are each 10.
6. A process of claim 1 wherein a, b are each 20.
7. A process of claim 1 wherein said effective glossing concentration is between 1% and 25% by weight.
8. A process of claim 1 wherein said effective glossing concentration is between 1% and 15% by weight.
9. A process of claim 1 wherein said effective glossing concentration is between is between 2% and 10% by weight.

* * * * *